United States Patent
Bannigan (10) Patent No.: US 12,150,864 B2
(45) Date of Patent: *Nov. 26, 2024

(54) EXPANDABLE INTERVERTEBRAL IMPLANT AND METHODS OF USE THEREOF

(71) Applicant: NuVasive, Inc., San Diego, CA (US)

(72) Inventor: Shaeffer Bannigan, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 314 days.

This patent is subject to a terminal disclaimer.

(21) Appl. No.: 17/696,540

(22) Filed: Mar. 16, 2022

(65) Prior Publication Data

US 2022/0202588 A1    Jun. 30, 2022

Related U.S. Application Data

(63) Continuation of application No. 16/405,714, filed on May 7, 2019, now Pat. No. 11,311,390, which is a continuation of application No. 15/792,104, filed on Oct. 24, 2017, now Pat. No. 10,322,010, which is a continuation of application No. 14/217,358, filed on Mar. 17, 2014, now Pat. No. 9,795,493.

(60) Provisional application No. 61/789,912, filed on Mar. 15, 2013.

(51) Int. Cl.
*A61F 2/44* (2006.01)
*A61F 2/30* (2006.01)
*A61F 2/46* (2006.01)

(52) U.S. Cl.
CPC .......... *A61F 2/447* (2013.01); *A61F 2/4455* (2013.01); *A61F 2002/30383* (2013.01); *A61F 2002/30471* (2013.01); *A61F 2002/30538* (2013.01); *A61F 2002/30579* (2013.01); *A61F 2002/30601* (2013.01); *A61F 2002/4415* (2013.01); *A61F 2002/4627* (2013.01); *A61F 2002/4629* (2013.01)

(58) Field of Classification Search
CPC .......... A61F 2/44; A61F 2/447; A61F 2/4415; A61F 2/4455; A61F 2/30; A61F 2/46
See application file for complete search history.

(56) References Cited

U.S. PATENT DOCUMENTS

| | | |
|---|---|---|
| 5,596,325 A | 1/1997 | Maas |
| 5,972,015 A | 10/1999 | Scribner |
| 6,193,757 B1 | 2/2001 | Foley et al. |

(Continued)

FOREIGN PATENT DOCUMENTS

| | | |
|---|---|---|
| CA | 2649107 | 10/2007 |
| EP | 2526882 | 11/2012 |

(Continued)

*Primary Examiner* — Christopher J Beccia (57) ABSTRACT

An expandable intervertebral implant including a first wall comprised of a male portion and a female portion in telescoping engagement with each other and a second wall comprised of a plurality of links, wherein the first wall and second wall are coupled to each other by hinges at each of the leading and trailing ends of the implant. The expandable implant is configured to be inserted into a disc space in a collapsed, narrow profile configuration and then unilaterally expanded in an anterior or posterior direction to a fully expanded, larger foot print configuration.

18 Claims, 13 Drawing Sheets

(56) References Cited

U.S. PATENT DOCUMENTS

| | | | |
|---|---|---|---|
| 6,641,614 B1 * | 11/2003 | Wagner | A61F 2/4455 623/17.15 |
| 7,854,766 B2 | 12/2010 | Moskowitz et al. | |
| 7,951,199 B2 | 5/2011 | Miller | |
| 8,109,972 B2 | 2/2012 | Zucherman et al. | |
| 9,138,328 B2 | 9/2015 | Butler | A61F 2/4425 |
| 9,795,493 B1 | 10/2017 | Bannigan | A61F 2/4455 |
| 10,322,010 B2 | 6/2019 | Bannigan | A61F 2/4455 |
| 11,311,390 B2 * | 4/2022 | Bannigan | A61F 2/4455 |
| 2002/0026197 A1 | 2/2002 | Foley et al. | |
| 2002/0151976 A1 | 10/2002 | Foley et al. | |
| 2004/0088054 A1 | 5/2004 | Berry | |
| 2004/0102774 A1 | 5/2004 | Trieu | |
| 2004/0133280 A1 | 7/2004 | Trieu | |
| 2004/0199168 A1 | 10/2004 | Bertagnoli et al. | |
| 2005/0043800 A1 | 2/2005 | Paul et al. | |
| 2005/0113920 A1 | 5/2005 | Foley et al. | |
| 2005/0174744 A1 | 8/2005 | Zheng | |
| 2005/0182417 A1 | 8/2005 | Pagano | |
| 2005/0256576 A1 | 11/2005 | Moskowitz et al. | |
| 2005/0261683 A1 | 11/2005 | Veldhuizen | A61F 2/4611 623/17.11 |
| 2006/0036241 A1 | 2/2006 | Siegal | |
| 2006/0074488 A1 | 4/2006 | Abdou | |
| 2006/0078428 A1 | 4/2006 | Zheng | |
| 2006/0089717 A1 | 4/2006 | Krishna | A61B 17/7064 623/17.11 |
| 2006/0142858 A1 | 6/2006 | Colleran et al. | |
| 2006/0241643 A1 | 10/2006 | Lim et al. | |
| 2007/0010845 A1 | 1/2007 | Gong et al. | |
| 2007/0067034 A1 | 3/2007 | Chirico et al. | |
| 2007/0073398 A1 | 3/2007 | Fabian et al. | |
| 2007/0118222 A1 | 5/2007 | Lang | |
| 2007/0260314 A1 | 11/2007 | Biyani | |
| 2007/0282449 A1 | 12/2007 | de Villiers et al. | |
| 2008/0082173 A1 | 4/2008 | Delurio et al. | |
| 2008/0208255 A1 | 8/2008 | Siegal | |
| 2008/0243251 A1 | 10/2008 | Stad et al. | |
| 2008/0243255 A1 | 10/2008 | Butler et al. | |
| 2008/0281346 A1 | 11/2008 | Greenhalgh et al. | |
| 2009/0076607 A1 | 3/2009 | Aalsma et al. | |
| 2009/0152061 A1 | 6/2009 | Tsai | |
| 2009/0157084 A1 | 6/2009 | Aalsma et al. | |
| 2009/0216331 A1 | 8/2009 | Grotz et al. | |
| 2009/0234454 A1 | 9/2009 | Siegal | |
| 2009/0248092 A1 | 10/2009 | Bellas et al. | |
| 2009/0281628 A1 | 11/2009 | Oglaza et al. | |
| 2010/0010633 A1 | 1/2010 | Kohm | |
| 2010/0161062 A1 | 6/2010 | Foley et al. | |
| 2010/0174373 A1 | 7/2010 | Galley et al. | |
| 2010/0198263 A1 | 8/2010 | Siegal et al. | |
| 2010/0262147 A1 | 10/2010 | Siegal et al. | |
| 2010/0286779 A1 | 11/2010 | Thibodeau | |
| 2010/0286783 A1 | 11/2010 | Lechmann et al. | |
| 2010/0292799 A1 | 11/2010 | Hansell et al. | |
| 2010/0292801 A1 | 11/2010 | Hansell et al. | |
| 2011/0093072 A1 | 4/2011 | Siegal | |
| 2011/0125270 A1 | 5/2011 | Paul et al. | |
| 2011/0184515 A1 | 7/2011 | Siegal | |
| 2011/0251689 A1 | 10/2011 | Seifert et al. | |
| 2011/0288646 A1 | 11/2011 | Moskowitz et al. | |
| 2011/0301712 A1 | 12/2011 | Palmatier | |
| 2012/0004732 A1 | 1/2012 | Goel et al. | |
| 2012/0071977 A1 | 3/2012 | Oglaza et al. | |
| 2012/0083887 A1 | 4/2012 | Purcell et al. | |
| 2012/0209386 A1 | 8/2012 | Triplett et al. | |
| 2012/0215313 A1 | 8/2012 | Saidha | |
| 2012/0215316 A1 | 8/2012 | Mohr et al. | |
| 2012/0259416 A1 | 10/2012 | Blackwell et al. | |
| 2012/0271422 A1 | 10/2012 | Miller et al. | |
| 2012/0290094 A1 | 11/2012 | Lim et al. | |
| 2012/0296433 A1 | 11/2012 | Farin | |
| 2012/0310048 A1 | 12/2012 | Siegal et al. | |
| 2012/0310350 A1 | 12/2012 | Farris et al. | |
| 2013/0035762 A1 | 2/2013 | Siegal et al. | |
| 2013/0041471 A1 * | 2/2013 | Siegal | A61B 17/3472 623/17.16 |
| 2013/0079883 A1 | 3/2013 | Butler | A61F 2/4465 623/17.16 |
| 2013/0103156 A1 | 4/2013 | Packer et al. | |
| 2013/0110239 A1 | 5/2013 | Siegal et al. | |
| 2013/0123924 A1 | 5/2013 | Butler et al. | |
| 2013/0158664 A1 | 6/2013 | Palmatier | A61F 2/447 623/17.16 |
| 2013/0158668 A1 | 6/2013 | Nichols et al. | |
| 2013/0166031 A1 | 6/2013 | Caratsch | |
| 2013/0190876 A1 | 7/2013 | Drochner et al. | |
| 2013/0274883 A1 | 10/2013 | McLuen et al. | |
| 2014/0031940 A1 | 1/2014 | Banouskou | |

FOREIGN PATENT DOCUMENTS

| | | |
|---|---|---|
| WO | WO2007/008568 | 1/2007 |
| WO | WO2012/115631 | 8/2012 |
| WO | WO2013/006669 | 1/2013 |

* cited by examiner

EXPANDABLE INTERVERTEBRAL IMPLANT AND METHODS OF USE THEREOF

CROSS REFERENCE TO RELATED APPLICATIONS

This application is a continuation of U.S. patent application Ser. No. 16/405,714, filed on May 7, 2019, which is a continuation of U.S. patent application Ser. No. 15/792,104 filed on Oct. 24, 2017 (now U.S. Pat. No. 10,322,010), which is a continuation of U.S. patent application Ser. No. 14/217,358, filed on Mar. 17, 2014 (now U.S. Pat. No. 9,795,493), which claims priority from U.S. Provisional Application No. 61/789,912, which was filed on Mar. 15, 2013. The entire contents of all of the foregoing are hereby incorporated by reference as a part of this application.

BACKGROUND

The present application relates to spinal fusion surgery, and more particularly, to an expandable intervertebral implant device.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The expandable intervertebral implant disclosed herein boasts a variety of inventive features and components that warrant patent protection, both individually and in combination.

FIGS. 1-7 illustrate an exemplary embodiment of an expandable intervertebral implant 10. The expandable intervertebral implant 10 includes a telescoping posterior wall 20 and an anterior wall 30. The posterior 20 and anterior 30 walls are connected by a hinge 40, 42 at the each of the leading end 12 and trailing end 14, respectively. The expandable intervertebral implant 10 has a length from the leading end 12 to the trailing end 14 dimensioned to span the width of the intervertebral disc space when the implant 10 is in its fully expanded state, i.e. the fully expanded implant is long enough, from leading end 12 to trailing end 14, to extend from the distal cortical bone lateral aspect to the proximal cortical bone lateral aspect of the vertebral bodies adjacent the disc space.

The implant comprises a telescoping posterior wall 20, formed of male 22 and female portions 24 (FIG. 2) and an anterior wall 30 formed of a plurality of links 32, 34, 36 coupled to each other and to the posterior wall 20 by a plurality of hinges 40, 42. The implant 10 is configured to be inserted into the intervertebral disc space via a lateral approach to the spine in its collapsed insertion state. In its collapsed state, the linked anterior wall 30 and the telescoping posterior wall 20 are generally parallel to each other in generally straight, linear configurations, respectively. In the collapsed state, the medial faces 21, 31 of the posterior wall 20 and anterior wall 30 are in close proximity to each other. According to the embodiment shown in FIG. 1, once the implant 10 is placed in the desired position within the disc space in its collapsed state, the implant 10 is expanded to the expanded state shown in FIG. 1 by displacing the anterior wall 30 anteriorly while the posterior wall 20 remains in a fixed position. According to this exemplary embodiment, an insertion tool (not shown) is used to position the implant 10 within the disc space and subsequently expand the implant 10. The insertion tool has a distal tip that engages the insertion tool aperture 13 (FIGS. 1-2) on the medial face 21 of the leading end of the anterior wall 20. Groove 25 along a substantial portion of the medial face 21 of posterior wall 20 and a groove (not shown) along a substantial portion of the medial face 31 of anterior wall 30 form a channel to accommodate the shaft of the insertion tool during insertion of the implant 10. The insertion tool is used to push the proximal end 14 of the implant 10 toward the distal end 12, causing the telescoping posterior wall 20 to decrease in length and the links 32, 34, 36 of the anterior wall 30 to pivot about the hinges 40, 41, 42, 43, thereby causing the width (i.e. the anterior to posterior dimension of the implant) to expand. Upon expansion, the implant 10 comprises a fusion aperture 50 (FIG. 1) bordered by the anterior 30 and posterior walls 20.

Figure 1:
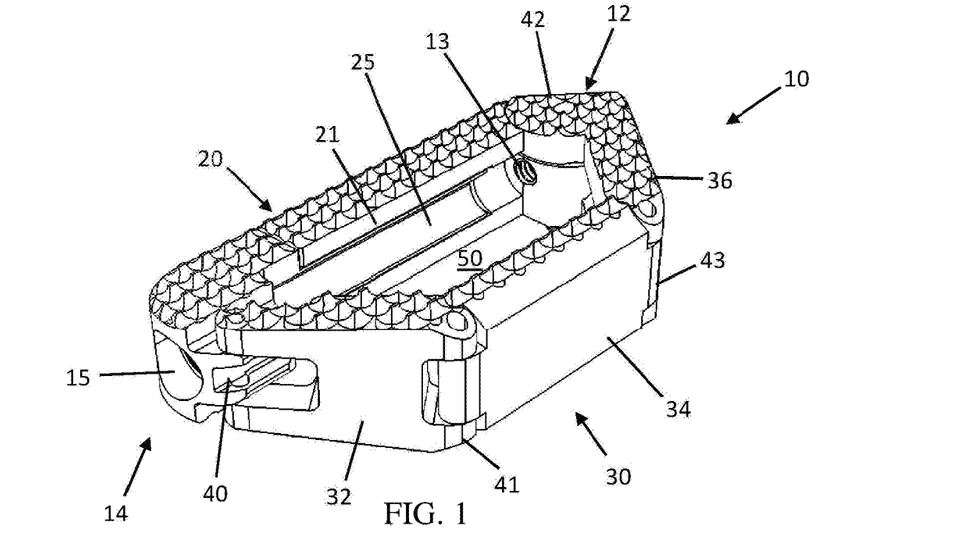
FIG. 1 is a perspective view of an exemplary embodiment of an expandable intervertebral implant in its fully expanded state.
Figure 2:
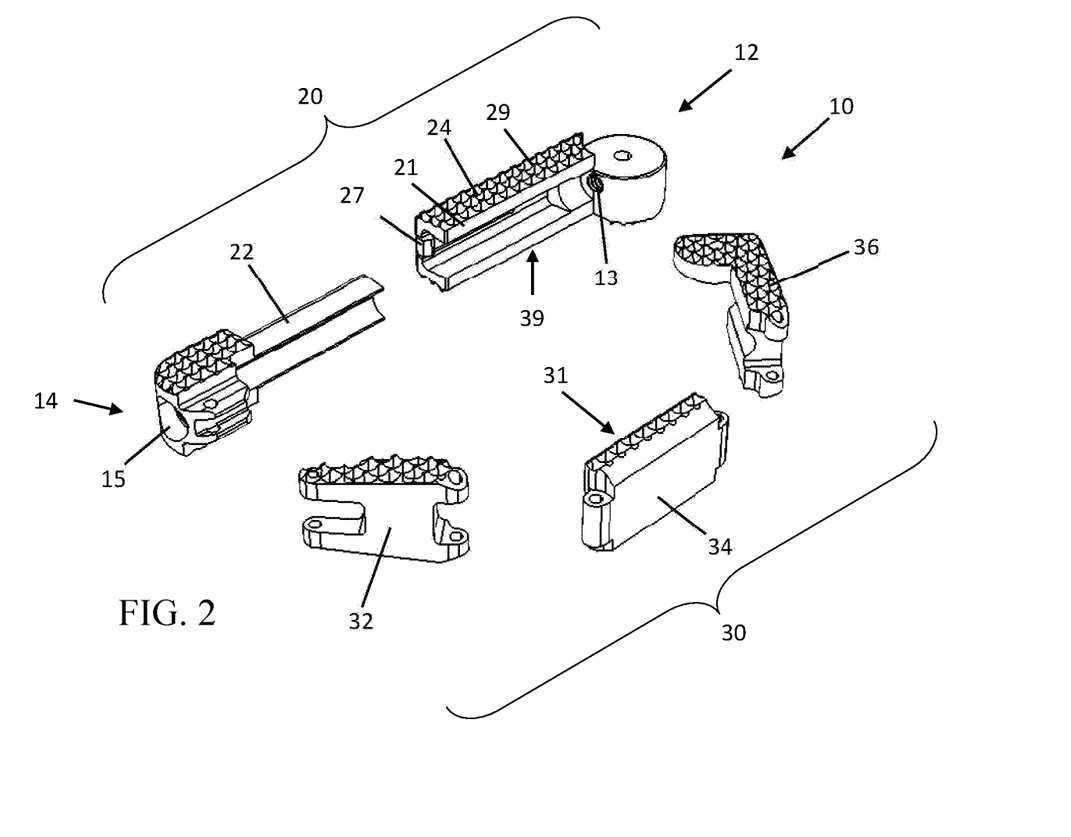
FIG. 2 is an exploded perspective view of the expandable intervertebral implant according to the exemplary embodiment of FIG. 1.
Figure 3:
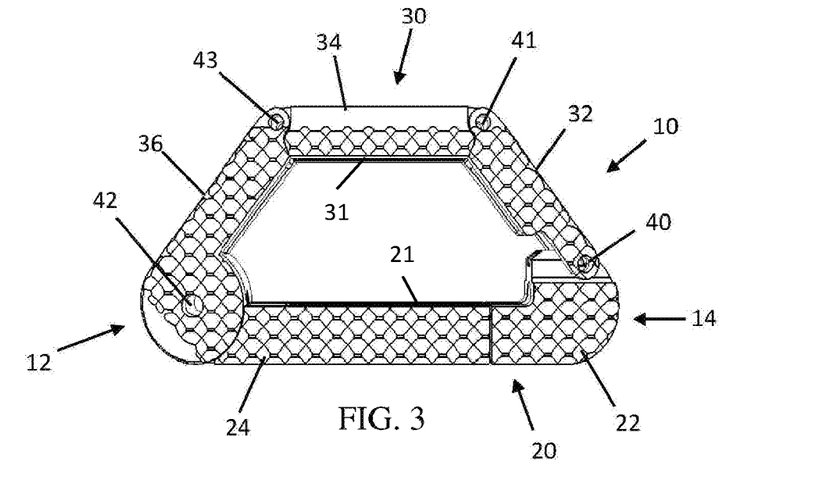
FIG. 3 is a top view of the expandable intervertebral implant according to the exemplary embodiment of FIG. 1.
Figure 4:
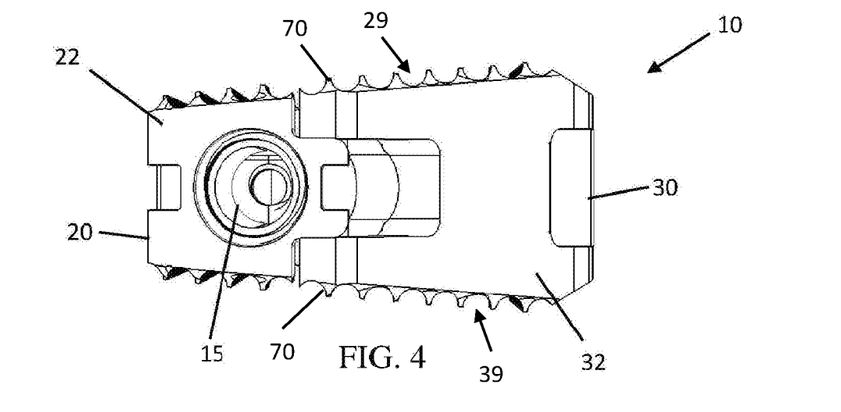
FIG. 4 is a lateral view of the trailing end of the expandable intervertebral implant according to the exemplary embodiment of FIG. 1.
Figure 5:
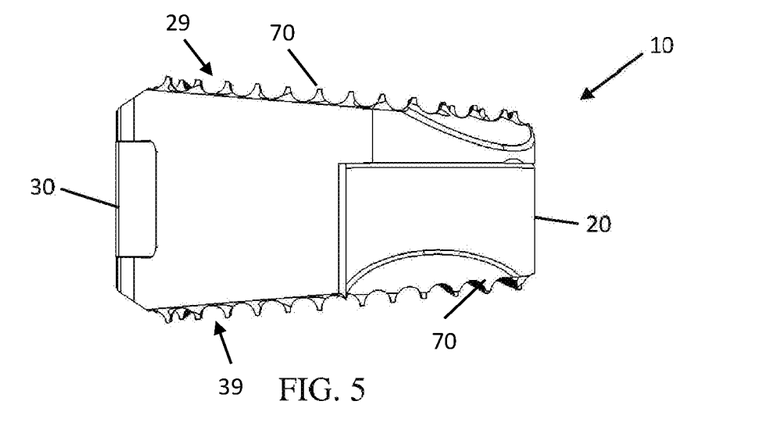
FIG. 5 is lateral view of the leading end of the expandable intervertebral implant according to the exemplary embodiment of FIG. 1.

FIG. 2 is an exploded perspective view of the expandable implant 10. The telescoping posterior wall 20 has a leading end 12 and a trailing end 14, and further includes a distal female portion 24 and a proximal male portion 22. The medial face 21 of the leading end 12 of the posterior wall 20 includes an aperture 13 for receiving the distal tip of an insertion tool (not shown). The proximal most end of the female portion 24 includes a mating feature 27 that complements a mating feature 26 (FIG. 7) at the distal most end of the male portion 22 such that when the implant 10 is fully expanded, the mating features 26, 27 engage to lock the implant 10 in the expanded state. The medial faces 21 of the male and female portions 22, 24 of the posterior wall 20 include a groove 25 (FIG. 1) to accommodate the shaft of the insertion tool. The trailing end 14 of the posterior wall 20 includes an insertion tool aperture 15 to receive the shaft of the insertion tool. The top and bottom surfaces 29, 39 of the posterior wall 20 are bone contacting surfaces that include anti-migration features 70 (FIGS. 4-5). The anterior wall 30 includes a plurality of links 32, 34, 36. The links 32, 34, 36 are configured to form a hinge 40, 41, 42, 43 at each end of the link 32, 34, 36. The distal most link 36 forms a hinge with the distal end of the posterior wall 20 and the proximal most link 32 forms a hinge 40 with the proximal end 14 of the posterior wall 20. According to the embodiment shown in FIGS. 1 and 2, the anterior wall 30 further comprises a middle link 34 hingedly coupled to the distal most link 36 and the proximal most link 32. The anterior wall 30 has top and bottom surfaces 29, 39 that are bone contacting surfaces including anti-migration features 70 (FIGS. 4-5).

Figure 6:
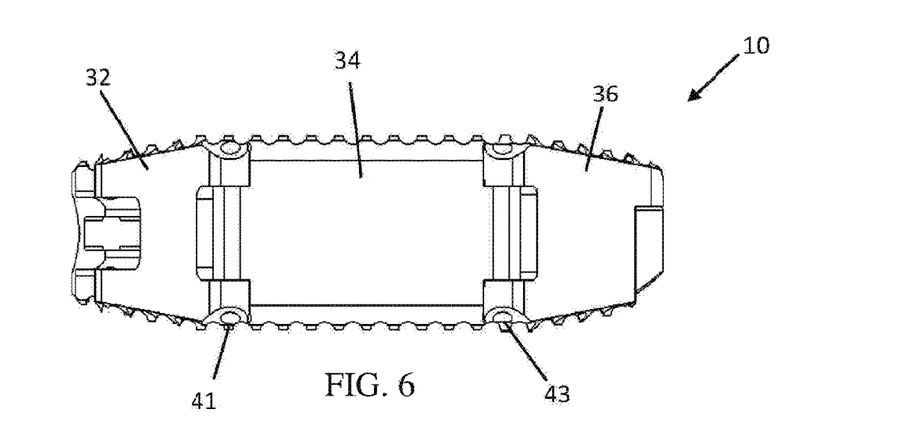
FIG. 6 is an anterior view of the expandable intervertebral implant according to the exemplary embodiment of FIG. 1.
Figure 7:
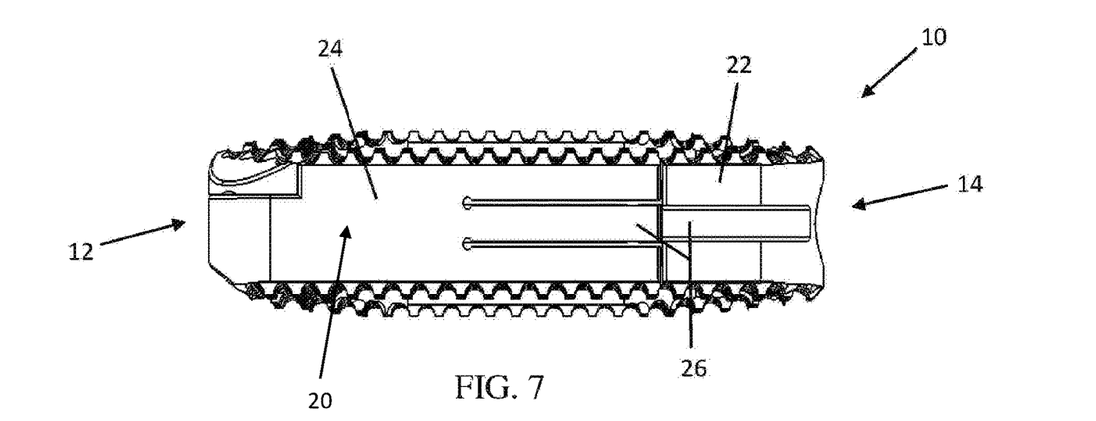
FIG. 7 is a posterior view of the expandable intervertebral implant according to the exemplary embodiment of FIG. 1.

As seen in FIGS. 4 and 5, according to this exemplary embodiment, the anterior wall 30 has a greater height than the posterior wall 20 to restore lordosis at the treated spinal level. Also demonstrated in FIGS. 4 and 5, the anti-migration features 70 on the top and bottom surfaces 29, 39 of the implant 10 according to this embodiment include a plurality of teeth. As best seen in FIG. 6, the middle link 34 may have a uniform height and the links 32, 36 connecting the posterior wall to the middle link change in height along the length of the link. As best seen in FIG. 7, according to this exemplary embodiment, the mating feature 27 (FIG. 2; not labeled on FIG. 7) on the female portion 24 of the posterior wall 20 is a deflectable tab that mates with a complementary recess (not shown) on the male portion 22 of the posterior wall 20.

Figure 8:
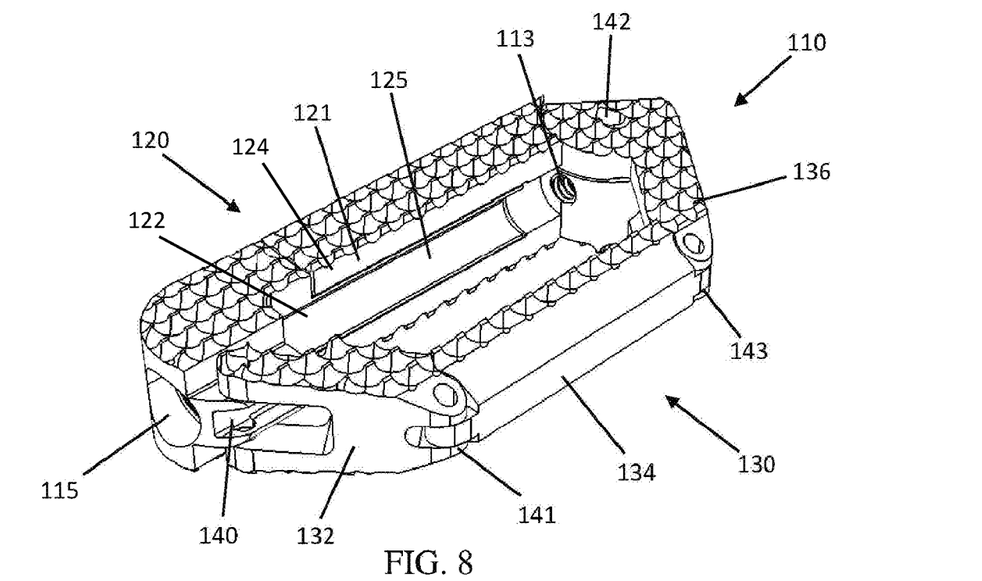
FIG. 8 is a perspective view of an alternative embodiment of an expandable intervertebral implant in its fully expanded state.
Figure 9:
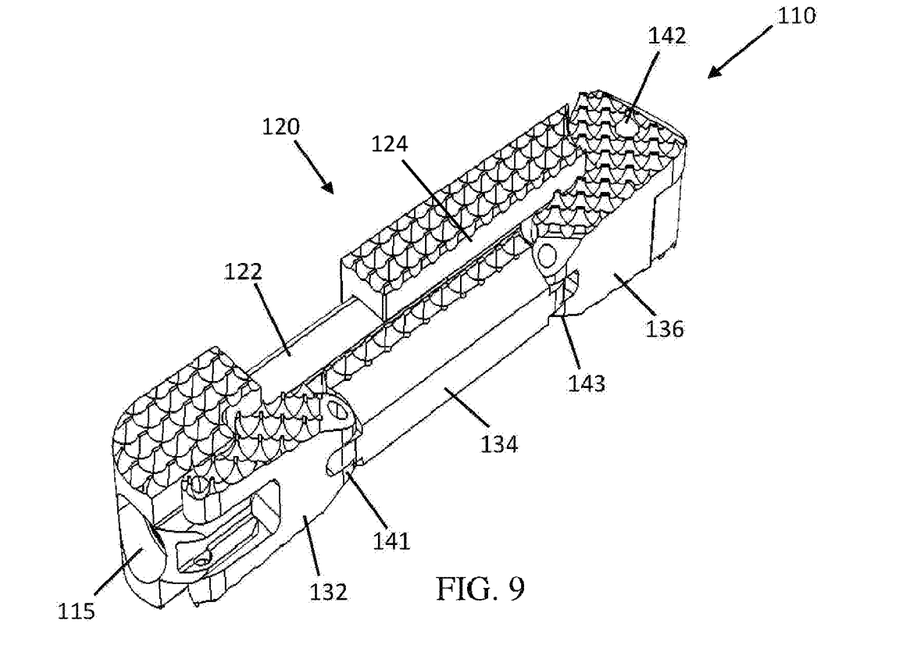
FIG. 9 is a perspective view of the alternative embodiment of the expandable intervertebral implant of FIG. 8 in its collapsed state.
Figure 10:
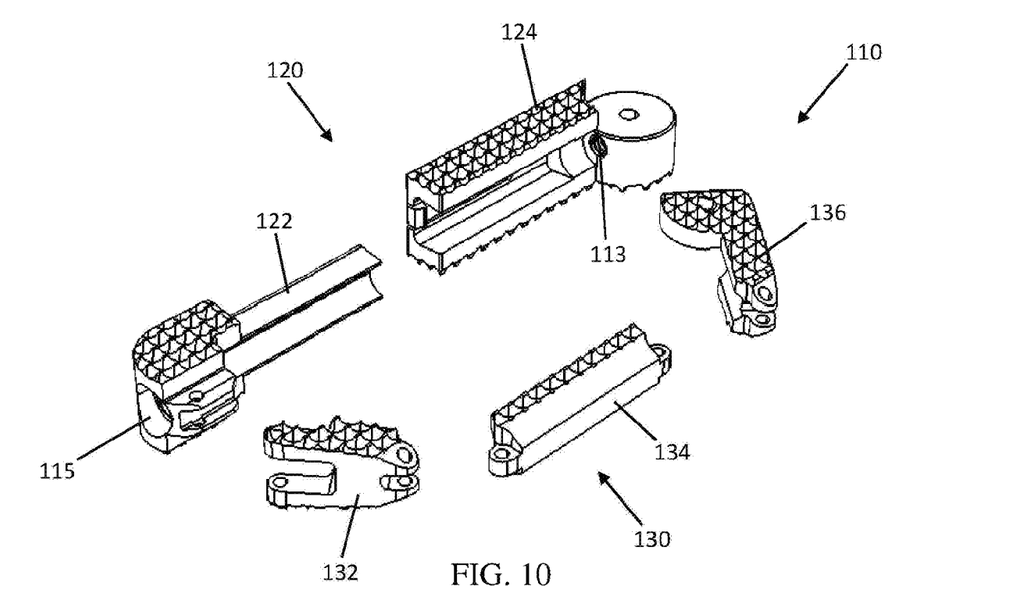
FIG. 10 is an exploded perspective view of the alternative embodiment of the expandable intervertebral implant of FIG. 8.
Figure 11:
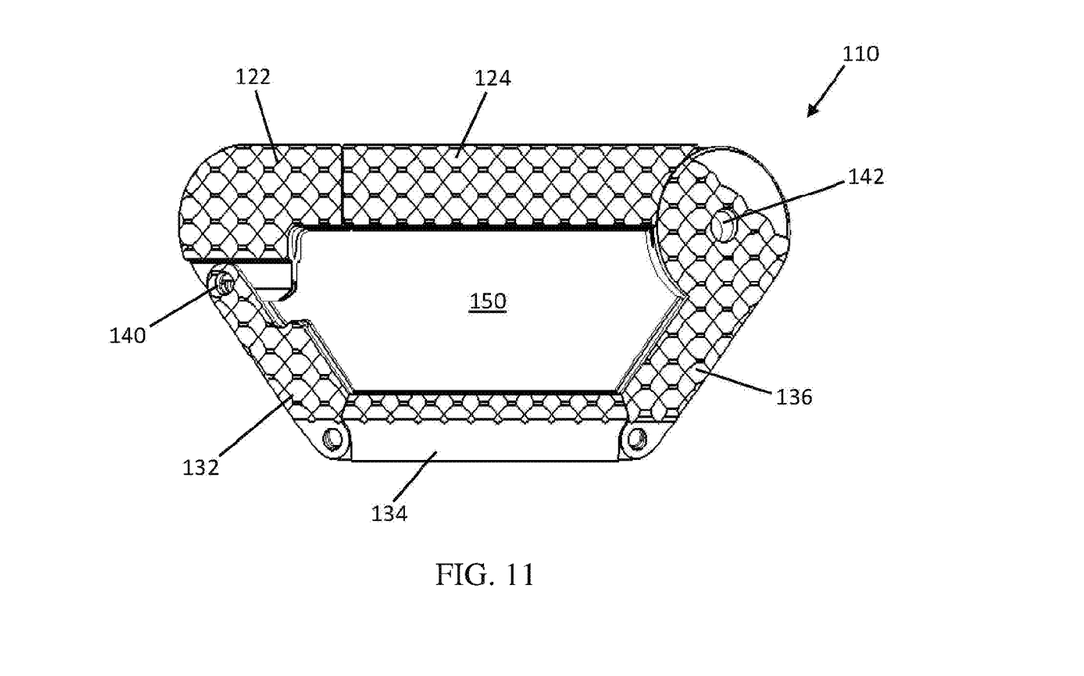
FIG. 11 is a top view of the expandable intervertebral implant of FIG. 8 in its fully expanded state.
Figure 12:
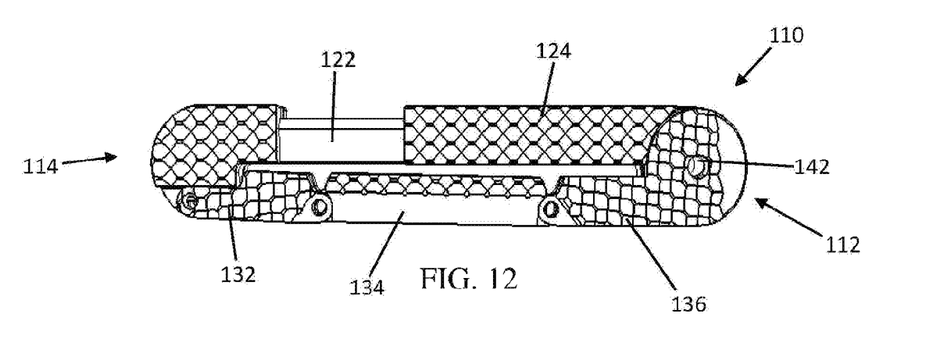
FIG. 12 is a top view of the expandable intervertebral implant of FIG. 8 in its collapsed state.
Figure 13:
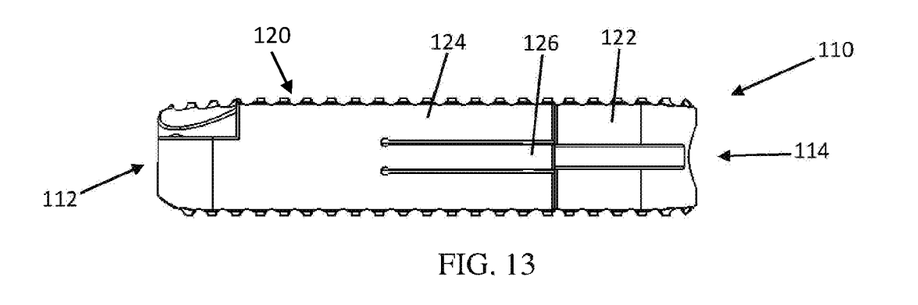
FIG. 13 is an anterior view of the expandable intervertebral implant of FIG. 8.
Figure 14:
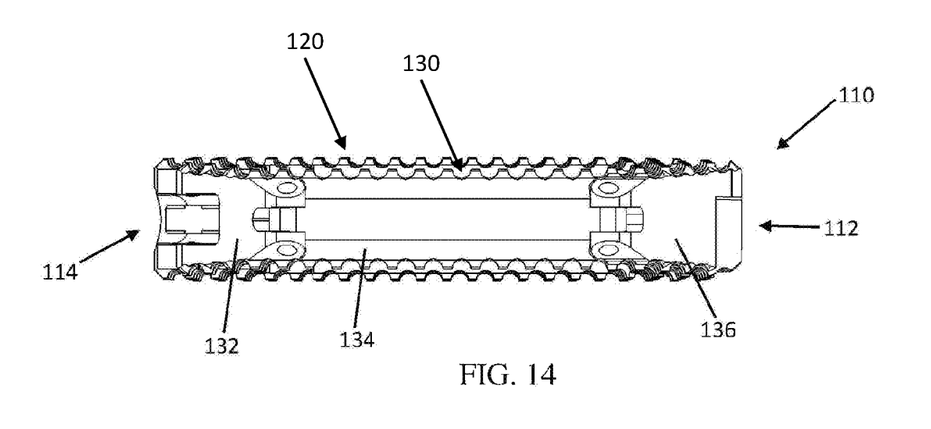
FIG. 14 is a posterior view of the expandable intervertebral implant of FIG. 8.
Figure 15:
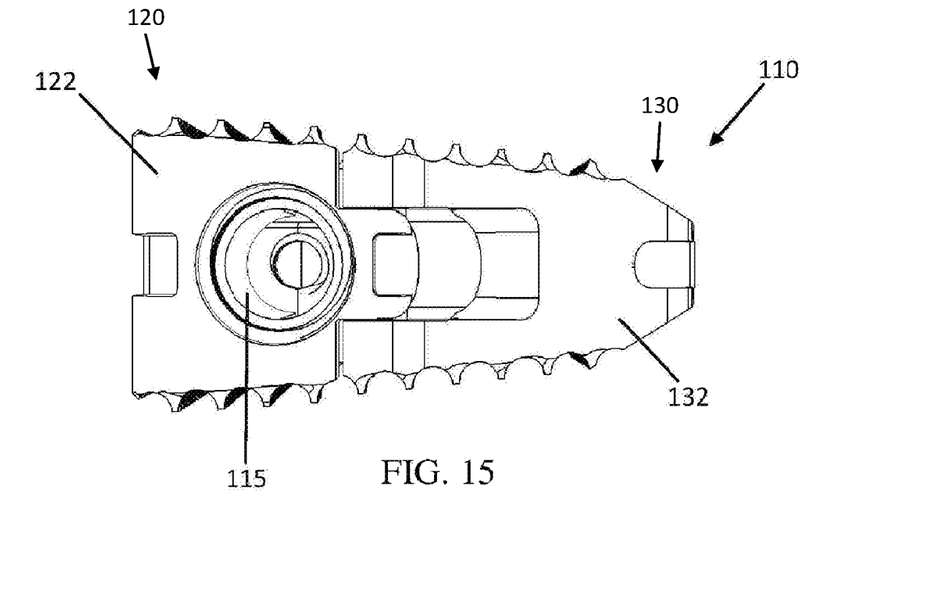
FIG. 15 is a lateral view of the leading end of the expandable intervertebral implant of FIG. 8.
Figure 16:
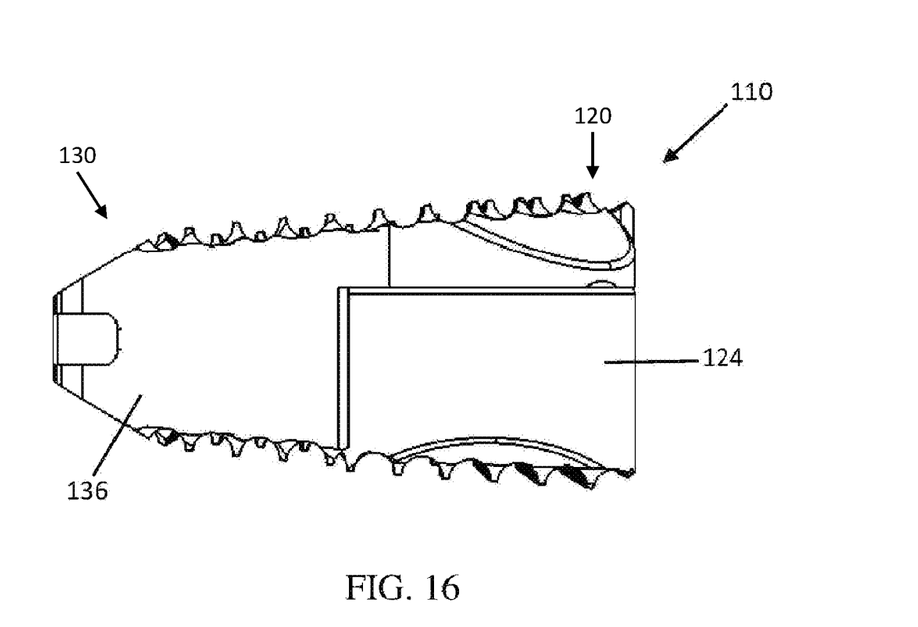
FIG. 16 is a lateral view of the trailing end of the expandable intervertebral implant of FIG. 8.

FIGS. 8-16 illustrate an alternative embodiment of an expandable intervertebral implant 110 having a leading edge 112 and a trailing edge 114. This alternative embodiment has all the same features and components described above for the exemplary embodiment of FIGS. 1-7, for example, insertion tool apertures 13, 15 (FIGS. 1-2) function similarly to insertion tool apertures 113, 115 (FIGS. 8-10), fusion aperture 50 (FIG. 1) functions similarly to fusion aperture 150 (FIG. 11), and so on. However, in the embodiment of FIGS. 8-16, implant 110 is configured to be inserted into an anterior portion of the disc space and then expanded in a posterior direction by displacing the posterior wall 130. As such, the anterior wall 120 is formed of a female portion 124 and the male portion 122 engaged in a telescoping relationship with each other (FIG. 9). As seen in FIGS. 8 and 9, the length of the overall anterior wall 120 is greater (and, consequently, the implant) when the implant 110 is in the collapsed insertion state (FIG. 9) than when the implant 110 is in the expanded state (FIG. 8). As can be seen from FIGS. 13-16, the anterior wall 120 of the implant 110 has a greater height than the posterior wall 130. The middle link 134 of the posterior wall 130 has a uniform height, and the links 132, 136 flanking the middle link 134 decrease in height from the hinge 140, 142 with the anterior wall 120 to the hinge with the middle link 141, 143.

Figure 17:
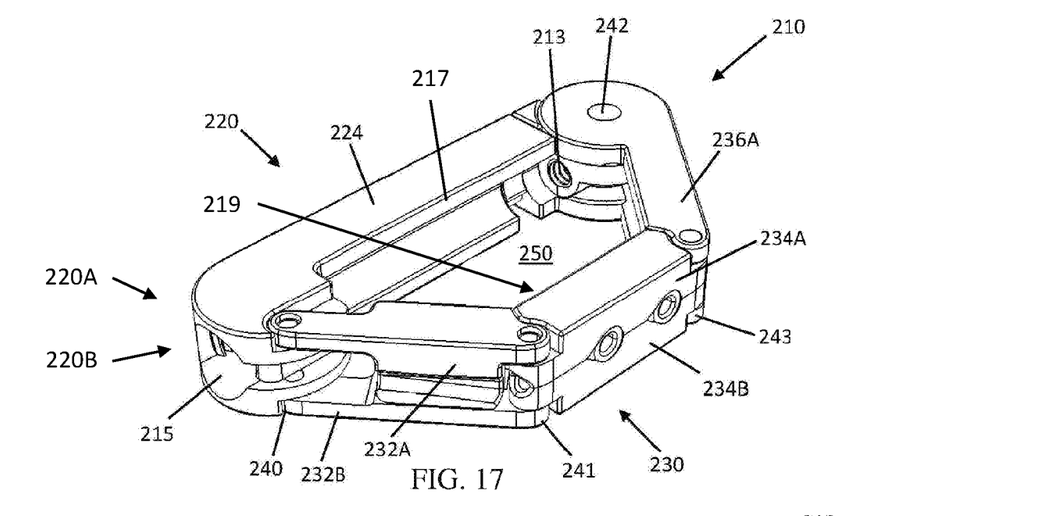
FIG. 17 is a perspective view of another alternative embodiment of an expandable intervertebral implant in its collapsed state.
Figure 18:
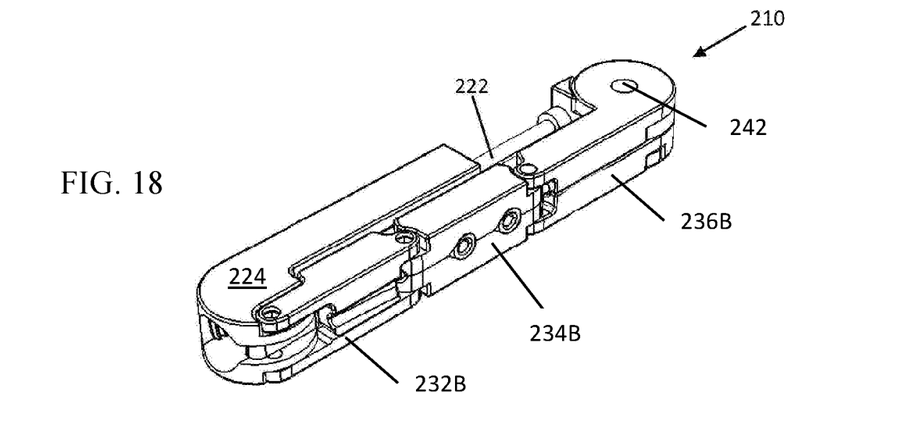
FIG. 18 is an anterior view of the expandable intervertebral implant of FIG. 17.

FIGS. 17-23 demonstrate another embodiment of an expandable intervertebral implant 210. The implant 210 according to this embodiment is unilaterally expandable in the anterior/posterior direction and the anterior wall 230 is also expandable in the cranial/caudal direction in order to restore lordosis at the spinal level being treated. The implant 210 according to this embodiment includes the same features and components as the previously described embodiments. For example, the implant 210 includes a telescoping posterior wall 220 formed of a male portion 222 (FIG. 18) that is received within a female portion 224 (FIG. 17). The anterior wall 230 is formed of a plurality of links 232, 234, 236. The method of anterior expansion according to this embodiment works the same way as previously described relative to implants 10 (FIGS. 1-7) and 110 (FIGS. 8-16), respectively. As demonstrated by FIGS. 17-19, the implant 210 is inserted into the disc space in its narrow profile collapsed insertion state (FIG. 18), then the proximal end 214 of the implant 210 is urged toward the distal end 212, causing the telescoping posterior wall 220 to decrease in length and thereby causing the linked anterior wall 230 to bend at the hinges 240, 241, 242, 243 as it expands anteriorly.

Figure 19:
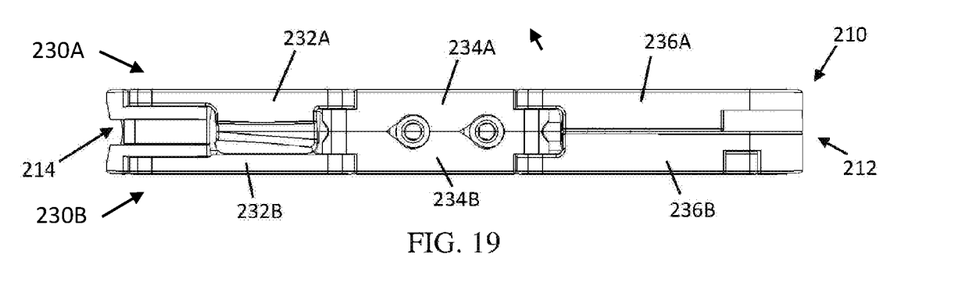
FIG. 19 is a perspective view of the expandable intervertebral implant of FIG. 17 in its anteriorly expanded state.
Figure 20:
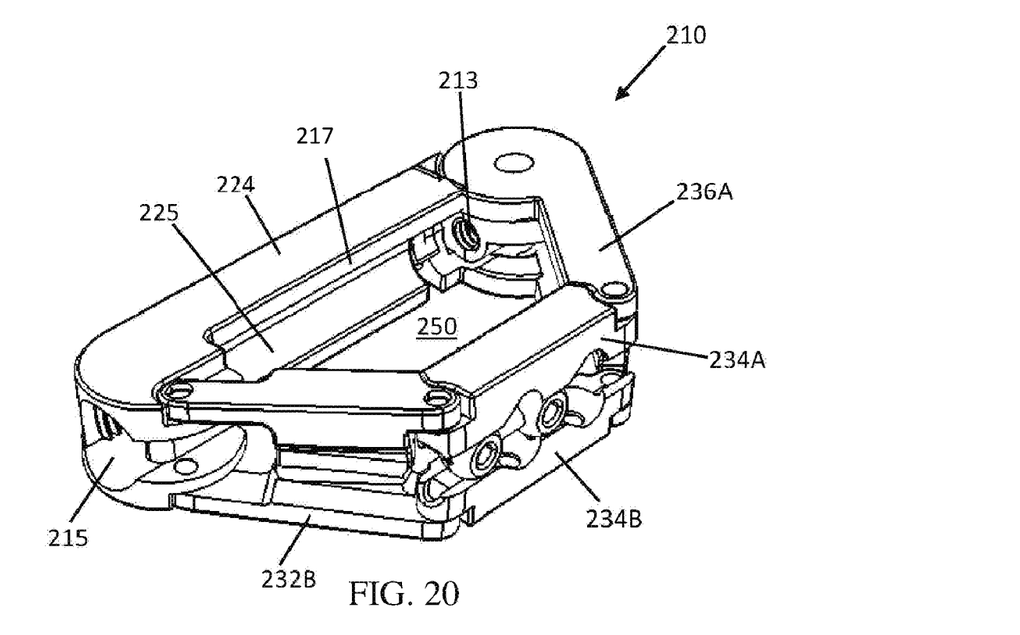
FIG. 20 is a perspective view of the expandable intervertebral implant of FIG. 17 in its fully expanded state.
Figure 21:
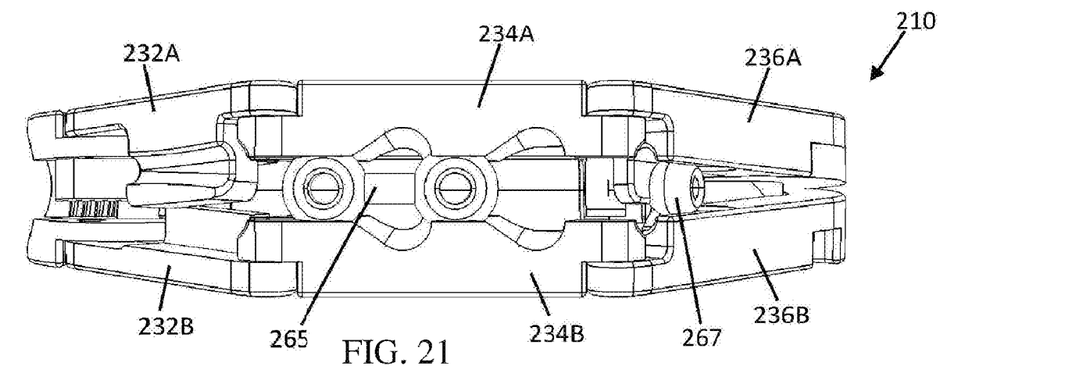
FIG. 21 is an anterior view of the expandable intervertebral implant of FIG. 17 in its fully expanded state.
Figure 22:
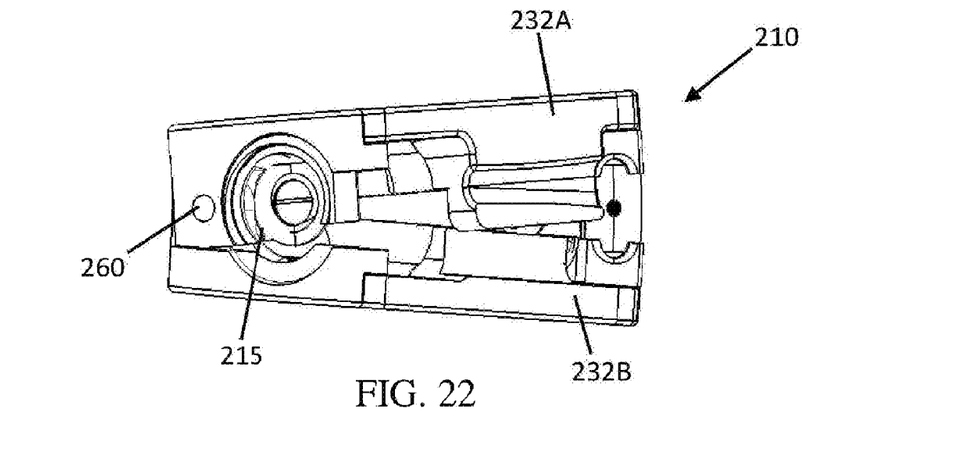
FIG. 22 is a lateral view of the trailing end of the expandable intervertebral implant of FIG. 17 in its fully expanded state.
Figure 23:
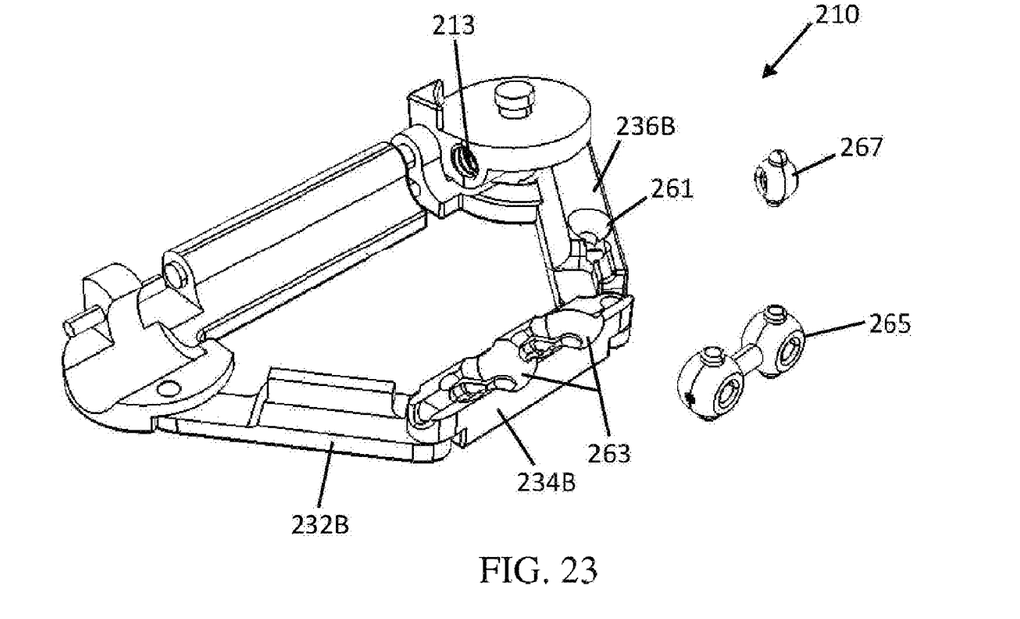
FIG. 23 is a partially exploded perspective view of the expandable intervertebral implant of FIG. 17.

FIGS. 20-22 show the implant 210 in its fully expanded state. In addition to the features of the previously described embodiments, the anterior and posterior walls 230, 220 according to this embodiment are separated into an upper portion 220A (FIG. 17), 230A (FIG. 19) and a lower portion 220B (FIG. 17) and 230B (FIG. 19). During insertion and anterior unilateral expansion of the implant 210, the medial surfaces 217, 219 of the top (A) and bottom (B) portions of the anterior and posterior walls 230, 220 are in contact with each other upon full lateral expansion, the top portion 220A, 230A of the implant 210 is rotated about a pivot point 260 (FIG. 22) in the posterior wall 220 of the implant 210, causing the top portion 230A of the anterior wall 230 to move away from the bottom portion 230B of the anterior wall 230. As best illustrated in FIG. 22, the displacement of the top portion 230A of the anterior wall 230 results in the implant 210 having a greater height at the anterior wall 230 than at the posterior wall 220. In the exemplary embodiment shown in FIGS. 17-23, the top portion 230A of the implant 210 is displaced by movement of a ball linkage 267 (FIGS. 21, 23) from a lower pocket 261 (FIG. 23) to an upper pocket 263 (FIG. 23). The ball linkages 265, 267 (FIG. 21) are coupled to a tensioning element (not shown), such as a cable or wire, which is coupled to and capable of manipulation through the insertion tool (not shown). Once the implant 210 has achieved its full anterior expansion, the tensioning member is manipulated to cause the ball linkages 265, 267 to travel from the lower pocket 261 up the ramp until the balls of the ball linkage 265, 267 settle into the upper pocket 263. The movement of the ball linkage 265, 267 lifts the upper portion 230A of the anterior wall 230, causing it to rotate about the pivot point 260 in the posterior wall 220 of the implant 210. Once the ball linkages 265 have settled in the upper pocket 263, the tension element is crimped to maintain the tension.

Figure 24:
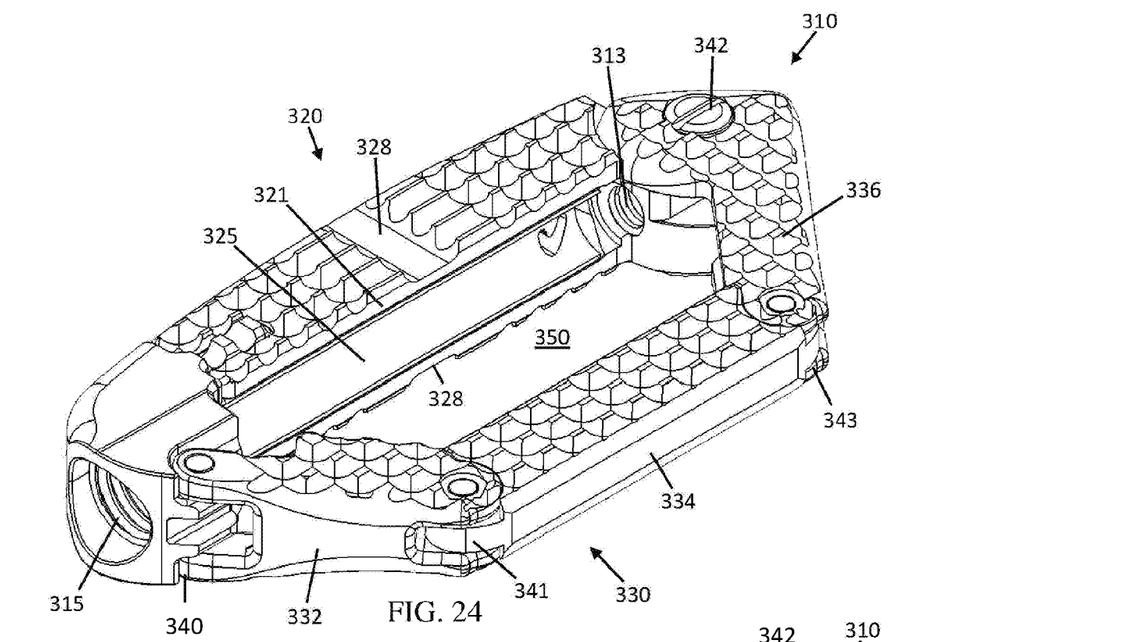
FIG. 24 is a perspective view of yet another alternative embodiment of an expandable intervertebral implant in its fully expanded state.
Figure 25:
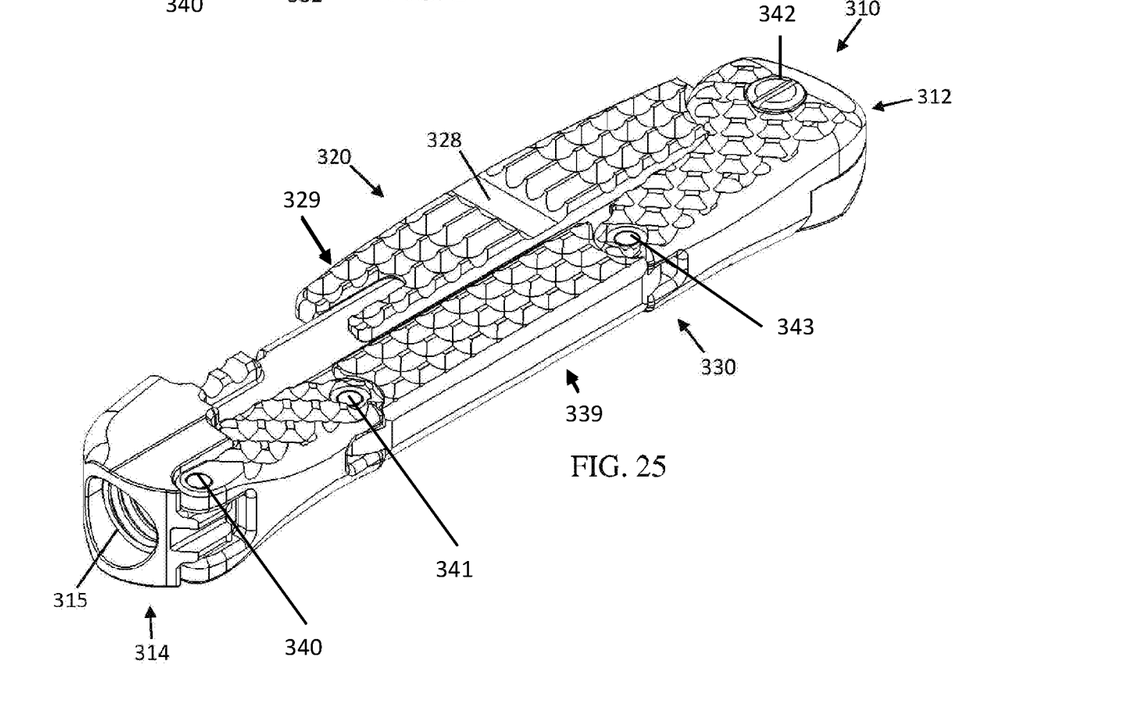
FIG. 25 is a perspective view of the expandable intervertebral implant of FIG. 24 in its collapsed state.
Figure 26:
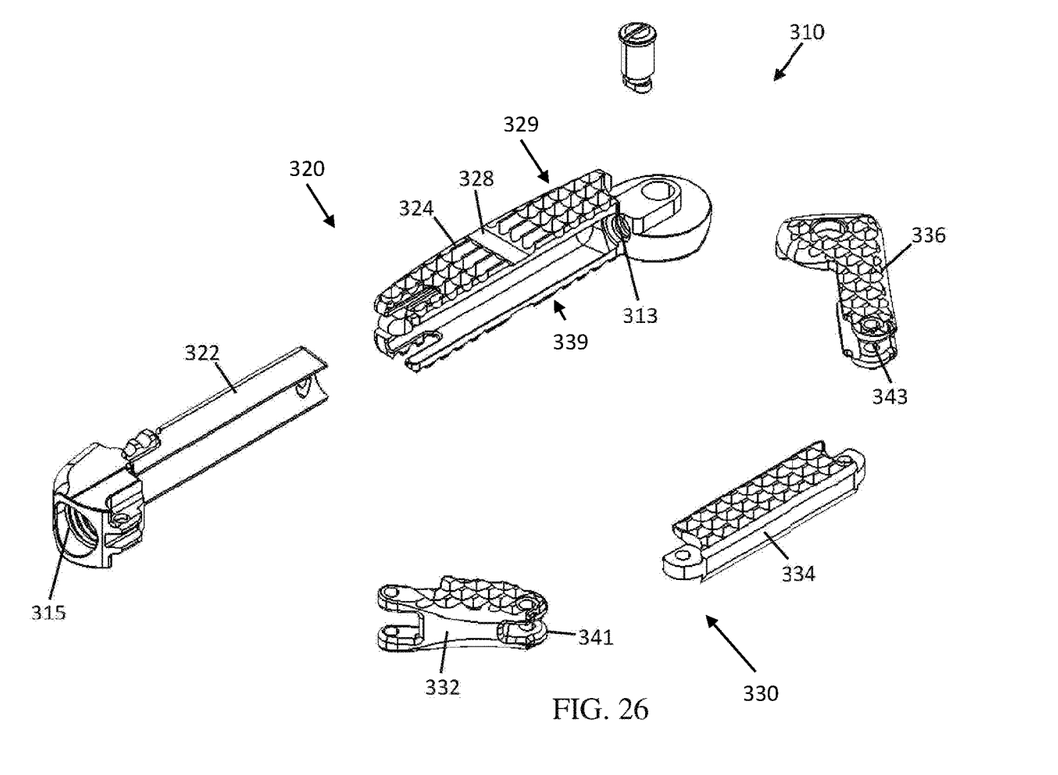
FIG. 26 is an exploded perspective view of the expandable intervertebral implant of FIG. 24.
Figure 27:
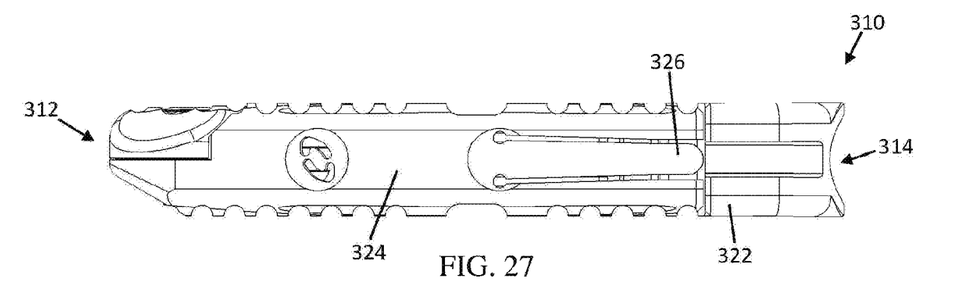
FIG. 27 is an anterior view of the expandable intervertebral implant of FIG. 24.
Figure 28:
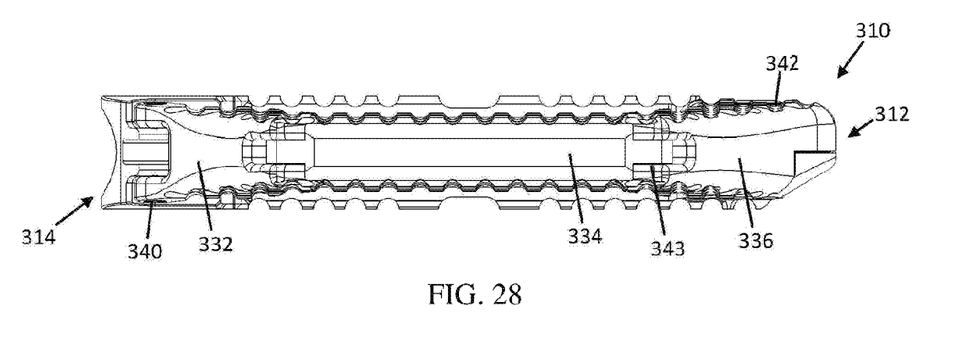
FIG. 28 is a posterior view of the expandable intervertebral implant of FIG. 24.

FIGS. 24-28 illustrate another alternative embodiment of an expandable intervertebral implant 310. The implant 310 according to this embodiment has the same components as described above relative to expandable implant 110, shown in FIGS. 8-16. As described above for the previous embodiment, the expandable vertebral implant 310 has a telescoping anterior wall 320 formed of a male portion 322 and a female portion 324 in sliding engagement with each other (FIG. 26). The telescoping anterior wall 320 includes a locking mechanism 326 (FIG. 27) to lock the male and female portions 322, 324 in place with respect to each other when the implant 310 has been expanded to its fully expanded configuration. The telescoping anterior wall 320 is coupled to a posterior wall 330 by a hinge 340, 342 at each of the leading and trailing ends 312, 314 of the implant 310, respectively (FIGS. 24-25). The posterior wall 330 is comprised of a plurality of links 332, 334, 336 that are connected at hinges 340, 341, 342, 343 to allow the footprint of the implant 310 to be expanded when the trailing end 314 of the anterior wall 320 is pushed toward the leading end 312 of the anterior wall 320. The decrease in length of the anterior wall causes the posterior wall 330 to bend at the hinges 340, 341, 342, 343 and allows the footprint of the intervertebral implant 310 to expand posteriorly. While the embodiment shown in FIGS. 24-28 has the same general structure of the implant 110 of FIGS. 8-16, the implant 310 of FIGS. 24-28 further include a recessed portion 328 (FIGS. 24-26) on the top 329 and/or bottom surface 339 of the anterior wall 320. The recessed portion 328 is located at the center portion of the length of the anterior wall 320 when the implant 310 is in its fully expanded configuration (i.e. when the male portion 322 and female portion 324 are engaged and locked). The recessed portion 328 can be used as a marker for the surgeon using fluoroscopy or other radiographic techniques to determine proper placement of the expandable intervertebral implant 310 within the disc space during the procedure or to confirm proper placement of the implant postoperatively.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. An expandable intervertebral implant comprising:
   a telescoping posterior wall having a length; and
   an anterior wall comprising a plurality of links, the anterior wall coupled to the telescoping posterior wall by a first hinge at a trailing end of the expandable intervertebral implant and a second hinge at a leading end of the expandable intervertebral implant,
   wherein the expandable intervertebral implant is configured to be inserted into a disc space of a patient in a first configuration and expanded into a second configuration by changing the length of the telescoping posterior wall,
   wherein the anterior wall is further configured to be expanded in a cranial/caudal direction,
   wherein a height of the anterior wall is adjustable, and
   wherein the anterior wall comprises an upper portion and a lower portion, the upper portion being configured to separate from the lower portion to adjust the height of the anterior wall.

2. The expandable intervertebral implant of claim 1, wherein, upon expansion in the cranial/caudal direction, the implant is configured to restore lordosis at a treated spinal level of the patient.

3. The expandable intervertebral implant of claim 1, further configured to be expandable in an anterior/posterior direction, from the first configuration to the second configuration.

4. The expandable intervertebral implant of claim 1, the plurality of links comprising: a first link, a second link, and a third link.

5. The expandable intervertebral implant of claim 4, wherein the first link is coupled to the first hinge and is coupled to the second link by a third hinge, and the third link is coupled to the leading end by the second hinge and to the second link by a fourth hinge.

6. The expandable intervertebral implant of claim 1, wherein, in the second configuration, the height of the anterior wall is configured to expand to a height greater than a height of the telescoping posterior wall.

7. The expandable intervertebral implant of claim 1, wherein, in the first configuration, a medial surface of the upper portion and a medial surface of the lower portion are in contact with one another.

8. The expandable intervertebral implant of claim 1, further comprising a pivot point disposed on the telescoping posterior wall, about which the upper portion of the anterior wall is configured to rotate away from the lower portion of the anterior wall to expand in the cranial/caudal direction.

9. The expandable intervertebral implant of claim 1, further comprising a ball linkage disposed between the upper portion of the anterior wall and the lower portion of the anterior wall,
   wherein the ball linkage is configured to move between a first, lower pocket and a second, upper pocket, thereby displacing the upper portion of the anterior wall.

10. The expandable intervertebral implant of claim 9, further comprising a ramp disposed between the first, lower pocket and the second, upper pocket, wherein the ball linkage is configured to move along the ramp.

11. The expandable intervertebral implant of claim 9, further comprising a tensioning element coupling the ball linkage to an insertion tool, wherein the tensioning element is configured to be manipulated using the insertion tool.

12. The expandable intervertebral implant of claim 11, wherein the tensioning element comprises a cable or a wire.

13. The expandable intervertebral implant of claim 12, wherein the tensioning element is configured to be crimped to maintain a tension on the ball linkage after the ball linkage has moved to the second, upper pocket, and displaced the upper portion of the anterior wall.

14. The expandable intervertebral implant of claim 4, wherein each of the first link, the second link, and the third link comprises an upper portion and a lower portion, the upper portion being configured to separate from the lower portion to adjust the height of the anterior wall.

15. The expandable intervertebral implant of claim 14, further comprising:
   a first, lower pocket disposed between the upper portion and the lower portion of the first link;
   a second, upper pocket disposed between the upper portion and the lower portion of the second link; and
   a ball linkage configured to move from the first, lower pocket to the second, upper pocket, thereby displacing the upper portion of the anterior wall.

16. The expandable intervertebral implant of claim 15, further comprising a ramp disposed between the first, lower pocket and the second, upper pocket, wherein the ball linkage is configured to move along the ramp.

17. The expandable intervertebral implant of claim 15, wherein a height of the anterior wall is adjustable, and
   wherein, in the second configuration, the height of the anterior wall is greater than a height of the telescoping posterior wall.

18. The expandable intervertebral implant of claim 1, wherein the anterior wall is configured to be expanded in the cranial/caudal direction while positioned in the second configuration.

* * * * *